United States Patent [19]

Parent et al.

[11] 4,013,404
[45] Mar. 22, 1977

[54] METHOD OF DYEING HAIR WITH INDOLINES, INDOLES AND INDAZOLES

[75] Inventors: Richard Alfred Parent, Fairport, N.Y.; Frank Fred Loffelman, Middlesex, N.J.

[73] Assignee: American Cyanamid Company, Stamford, Conn.

[22] Filed: Apr. 7, 1975

[21] Appl. No.: 565,883

Related U.S. Application Data

[63] Continuation of Ser. No. 96,224, Dec. 6, 1970, abandoned.

[52] U.S. Cl. .......................................... 8/11; 8/10; 8/10.1; 8/10.2
[51] Int. Cl.$^2$ ................ D06P 1/32; D06P 3/06; A61K 7/12
[58] Field of Search .............. 8/11, 10, 10.1, 10.2

[56] References Cited
UNITED STATES PATENTS 3,194,734  7/1965  Seemuller ..................... 167/88

FOREIGN PATENTS OR APPLICATIONS 1,804,066  9/1969  Germany
1,916,139  11/1969  Germany
887,579  1/1962  United Kingdom

OTHER PUBLICATIONS

Venkataraman, "The Chemistry of Synthetic Dyes" (Academic Press, 1971), vol. V, pp. 475–534.
Rattee and Breuer, "The Physical Chemistry of Dye Adsorption" (Academic Press, 1974), pp. 295–297.

*Primary Examiner*—Joseph L. Schofer
*Assistant Examiner*—A.L. Clingman
*Attorney, Agent, or Firm*—Charles J. Fickey

[57]        ABSTRACT

A method for dyeing hair and other keratinaceous materials with certain amino, hydroxy, methoxy and nitro-containing indoline, indole and indazole compounds, and combinations thereof, and keratinaceous fibers dyed therewith.

7 Claims, No Drawings

METHOD OF DYEING HAIR WITH INDOLINES, INDOLES AND INDAZOLES

This is a continuation, of application Ser. No. 96,224, filed Dec. 6, 1970, now abandoned.

This invention relates to a method for dyeing hair and other keratinaceous materials with certain known and novel indoline, indole and indazole compounds.

Especially this invention relates to dyeing hair, by oxidative or direct method, using appropriately, as taught, one or more compounds of the formula

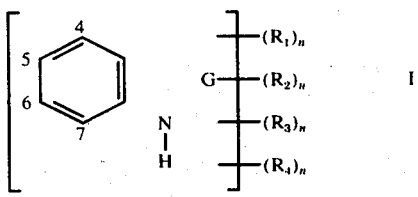

wherein G is a member selected from the divalent groups $-CH_2-CH_2-$;

where R is selectively H or lower alkyl, and $-N=CH-$ the nitrogen of which is attached to the cyclic

$R_1$ is hydrogen or amino; $R_2$ is hydrogen or nitro and $R_3$ is hydrogen, hydroxy or methoxy and at least one of $R_1$, $R_2$, and $R_3$ must be other than hydrogen; $n$ is selectively 1 or 2; and salts of such compounds with strong acids.

These compounds dye hair and other keratinaceous fibers, yellow to orange to red to brown shades.

Heretofore, dyes for hair and other keratinaceous fibers have been deficient in one or more properties. Such hair dyes lacked strength, attractive hue or shade, fastness to washing, fastness to crocking, fastness to light, or "build-up" "on tone." As an example of the latter, a brown dye may become redder with time or dyeing or with increased concentration of dye applied, instead of properly building up on tone. There is an ever present demand for new hair dyes, both oxidation and direct, and modifiers therefor, which correct these aforementioned deficiencies.

In accordance with the present invention, it has been found that hair and other keratinaceous fibers may be dyed with certain heterocyclic azole compounds represented by Formula I and above and further subgenerically divided into three classes, indolines, indoles and indazoles. These are represented by formulas II, III and IV below. In each subgeneric class are oxidation dyes, modifiers and direct dyes. These give attractive yellow to orange to red to brown shades, including drab and dark browns on hair.

Accordingly, an object of this invention is a method of dyeing hair with an indoline of the formula

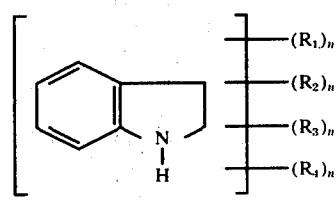

where $R_1$, $R_2$, $R_3$ and $R_4$ and $n$ are defined as above, and salts thereof.

Compounds illustrative of this class are: 5-, 6- and 7-aminoindolines and their salts, especially hydrochloride salts, 5-hydroxyindoline and its monohydrochloride salt, 5,6- and 5,7-diaminoindolines and their hydrochloride salts, 5-amino-6-nitroindoline and its hydrochloride salts, 5-bromo-7-nitroindoline and its hydrochloride salts and 6-nitroindoline and its salts.

Another object of this invention is a method of dyeing hair with an indole of the formula

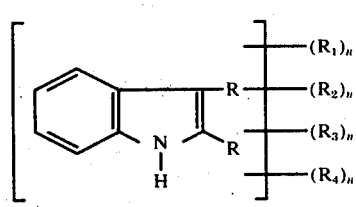

wherein R, $R_1$, $R_2$, $R_3$ and $R_4$ and $n$ are defined as above, and salts thereof.

Compounds illustrative of this class are 5-, 6-, or 7-aminoindoles and their salts, 5-amino-2,3-dimethylindole, 5-hydroxyindole, 5-hydroxy-2,6-dimethylindole, 5-hydroxy-2-methylindole, 5- and 7-methoxyindole, 5-methoxy-2-methylindole and the salts of these, and 6-nitroindole.

Another object of this invention is a method of dyeing hair with an indazole of the formula

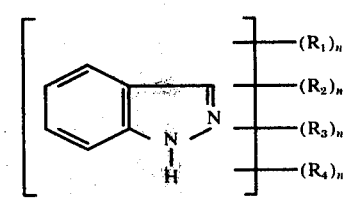

wherein $R_1$, $R_2$, $R_3$ and $R_4$ and n are defined as above, and salts thereof.

Compounds illustrative of this class are 5-, 6- and 7-aminoindazole and their salts, 5,6-diaminoindazole and its salts, and 5,6-dinitroindazole.

Except for three novel compounds and their salts, preparation of which is given in Examples 7, 8 and 9, i.e., respectively, 5-amino-6 -nitroindoline, 5,6-diaminoindoline and 5,7-diaminoindoline and their salts, the compounds are well known and their syntheses are given in the literature.

There are within each class of compounds II, III and IV, oxidation dyes and their modifiers, and direct dyes. One or more of such compounds may be used in the dyeing process or method of this invention. Those compounds where $R_1$ is amino and $R_2$ is hydrogen are oxidation dyes. Modifiers have $R_3$ as hydroxy or methoxy and $R_2$ hydrogen and may have an amino group; Direct dyes have at least one $R_2$ nitro group.

The oxidation dyes used in the method of this invention may be used not only with the modifiers of this invention but with known modifiers such as resorcinol, phloroglucinol, p-hydroxyanisole, pyrogallol, o-m- or p-amino-phenol and the like. Conversely the modifiers of this invention may be used with known oxidation hair dyes such as the phenylene diamines, toluylene diamines, polyaminophenols, polyaminopyridines and the like. The dyes of this invention may be used in the form of their bases or salts, the preferred salts being the mono or dihydrochlorides.

In oxidation dyeing, the dye in an amount 0.05 to 6%, is applied at ambient temperature from an alkaline aqueous composition, to the keratineous material be it human hair, animal fur, bristles, feather, wool and the like. A typical composition for hair dyeing may optionally have, in addition to the dye and water, 0.05 to 10% modifier as above; 0.1 to 0.5% antioxidant such as sodium sulfite, 0.5 to 15% surfactants such as alkylphenolpoly(ethyleneoxide), triethanolamine lauryl sulfate, 5 to 15% solvents such as benzyl alcohol, butanol, isopropanol and the like; also multipurpose agents which not only condition the hair, but solubilize dyes, increase viscosity, etc., of which two preferred ones are 10 to 20% oleic acid and 5 to 20% oleyl alcohol; a chelating agent may be used to remove trace metals such as iron which interfers with the method, as for example ethylenediaminetetraacetic acid disodium salt; 2 to 5% foam booster such as the alkanolamines might be used in addition to the above surfactant; also perfumes; the above is alkalized preferably with an excess of concentrated ammonium hydroxide solution or other alkali such as alkali or alkaline earth hydroxides, carbonates or bicarbonates, aliphatic low molecular weight amines, alkanolamines, heterocyclic amines such as morpholine; the hair dye composition thus obtained is stable and may be stored before use. In use, it is first diluted with an equal volume of a solution containing an oxidant such as hydrogen peroxide to give preferably 0.5 to 3% concentration of hydrogen peroxide; other oxidants such as urea peroxide, melamine peroxide, persulfates, perborates, percarbonates, bromates and the like may be used. The pH is adjusted to 7.5 to 9.0 if need be.

Hair or other keratinaceous fiber or material is immersed therein for 5 to 10 or more minutes depending upon the depth of shade desired, removed, shampooed and dried. With this method of dyeing, depending upon the compound or compounds selected, keratinaceous fibers and especially hair are dyed soft shades of ash blond and light browns to orange, reddish brown and other browns such as chestnut and dark browns.

In direct dyeing of hair and other keratinaceous fibers, 0.05 to 5% dye is dissolved in 5 to 15% organic solvents similar to the ones listed above, with 2 to 10% surfactant; 1 to 5% benzyl alcohol is desirable for its hair-penetrating ability; 0.25 to 0.5% chelating agent is also desirable; the remainder is water to 100% counting adjustment of the pH to between 4 and 9, and perfume. This composition is stable; the hair or other keratinaceous fiber is treated therewith at ambient temperature until the desired depth of shade is obtained, rinsed, shampooed and dried; yellow to orange to reds to browns are thus obtained.

By such methods for dyeing hair with the compounds new to this use, there are obtained attractive shades of good fastness.

The following examples illustrate this invention.

EXAMPLE 1

Oxidation hair dyeing with 6-aminoindoline dihydrochloride

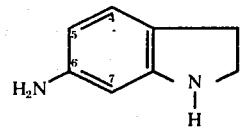

A. To a solution of 17 parts of a nonionic surfactant, nonylethanolpoly(ethylene oxide) in 25.4 parts of water at 50°–60° C. is added 0.1 part sodium sulfite, 6 parts 6-aminoindoline dihydrochloride, a known compound prepared by A. P. Terentier, et al., J. Gen. Chem. USSR 29 2504 (1959), and known modifiers consisting of 0.4 part o-aminophenol, 1.6 part pyrocatechol, 0.6 part phloroglucionol and 0.4 part 2,4-diaminoanisole hydrogen sulfate salt. The whole is stirred at 50°–60° C. for 15 minutes and cooled to ambient temperature.

B. A separate solution is prepared using 18 parts isopropanol as solvent for 18 parts oleyl alcohol, 8 parts oleic acid and 0.5 part of the above nonionic agent.

C. Five parts of concentrated 28–30% ammonium hydroxide solution.

D. Solution B is added to Solution A, and after stirring A + B, Solution C is added.

E. An equal portion, i.e., 100 parts, of 6% hydrogen peroxide solution is added to D.

F. The whole is divided into four parts. To each part is added a tress of albino hair and the hair held in the solution for a specific time, 10, 20, 30 and 40 minutes respectively, for the four parts. The hair from each part is rinsed, washed with dilute shampoo, rinsed and dried. After 10 minutes, the hair is an attractive medium golden brown shade. With 20, 30 and 40 minutes, the hair becomes progressively darker on tone.

If in the above procedure, 6-aminoindoline dihydrochloride is replaced by 5-aminoindoline dihydrochloride and a slight change made in modifiers to 1.6 parts o-aminophenol, 0.4 part pyrocatechol, 0.8 part phloroglucinol and 0.8 part 2,4-diaminoanisole hydrogen sulfate, the rest of the procedure being the same, hair is dyed a medium yellow brown in 10 minutes. After 20 minutes the hair is darker on tone; in 30 and 40 minutes the hair becomes progressively darker and redder.

If in the above procedure, 6-aminoindoline dihydrochloride is replaced by 6-aminoindole, brown shades of good color value are obtained, the 40 minute shade being a very drak brown.

EXAMPLE 2

Oxidation hair dyeing with 5-aminoindoline dihydrochloride

A solution composition is prepared by stirring together with 17.5 parts of water, 2 parts 5-aminoindoline dihydrochloride, a known compound prepared by A. Richardson, J. Org. Chem. 30 2583 (1965), plus

| | | |
|---|---|---|
| 20 | parts | octylphenolpoly(ethylene oxide) |
| 8 | parts | oleyl sarcosine |
| 8 | parts | N,N-diethyltoluamide |
| 4 | parts | lauryl diethanolamide |
| 0.5 | part | nonylphenolpoly(ethylene oxide) |
| 0.1 | | sodium sulfite |

To this is added 100 parts 6% hydrogen peroxide solution.

Albino hair immersed in this solution for 10 minutes is dyed a medium golden brown of good color value.

If in the above solution composition, 5-hydroxyindoline hydrochloride is used instead of the 5-aminoindoline.diHCl, albino hair is dyed a light brownish yellow. This compound is useful as a modifier. It is prepared by the procedure of R. Hunt, et al., J. Chem. Soc., 344 (1966).

If in the above solution composition, instead of 5-aminoindoline.diHCl, 6-aminoindole is used (of Example 3) albino hair is dyed a light neutral brownish orange shade. The 6-aminoindole is prepared by a method of R. K. Brown, et al., JACS 76 5149 (1954).

EXAMPLE 3

Oxidation hair dyeing with 5-aminoindole

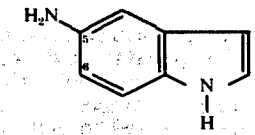

A solution composition is prepared by mixing with 59 parts water at 50°-60° C. until clear,

| | |
|---|---|
| 6 parts | 5-aminoindole, prepared as in Terentier, et al., idem of Example 1. |
| 10 parts | N,N-diethyltoluamide |
| 10 parts | octylphenolpoly(ethylene oxide) |
| | and on cooling to ambient temperature, |
| 5 parts | concentrated 28–30% ammonium hydroxide solution |

To the dye solution composition obtained, equal parts of 6% hydrogen peroxide solution are added. The resultant solution is divided into three parts, a tress of albino hair placed in each, and the hair dyed for 10, 20 and 30 minutes respectively. The hair is then removed, rinsed, shampooed, rinsed and dried. Red brown shades, all on tone, are obtained. The first, at 10 minutes, is a medium red-brown, at 20 minutes, a full red-brown and at 30 minutes, a dark red-brown.

When 1 part of 5-aminoindole is modified with 1 part of 5-hydroxy-2-methyl indole using the procedure of Example 4, a medium chestnut brown is obtained which darkens on tone when dyed for 30 minutes.

EXAMPLE 4

Oxidation hair dyeing with 5-aminoindazole

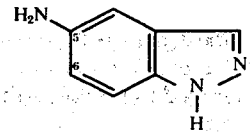

A liquid dye composition is prepared by mixing 8 parts of a cationic surfactant, polyethoxylated oleyl methyl ammonium chloride, with 83 parts of water and to it adding 1 part 5-aminoindazole dissolved in 8 parts butanol. The resultant solution is mixed with an equal quantity of 6% hydrogen peroxide solution to give the dye composition.

Albino hair tresses immersed in this dye composition are dyed an orange of good color value.

When half the 5-aminoindazole in the above procedure is replaced with a modifier of this invention 5-hydroxyindole, an attractive light-brown shade on hair is obtained.

The addition of 1 part of resorcinol, a known modifier to the above using 82 parts water, results in attractive light golden brown hair.

EXAMPLE 5

Oxidation hair dyeing with 5-amino-2,3-dimethylindole

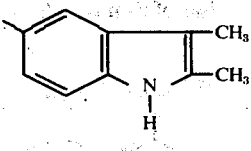

A hair dyeing composition is prepared by mixing 8 parts of the cationic surfactant of Example 4 with 80 parts water and to it adding 3 parts 5-amino-2,2-dimethylindole [prepared by the method of H. Bauer, et al., Ber. 65 308 (1932)] and 1 part resorcinol, both dissolved in 8 parts butanol. The resultant solution is mixed with an equal quantity of 6% hydrogen peroxide solution.

Albino tresses immersed in this dye composition for 10 minutes are dyed an attractive golden brown of good color value.

The self-shade, without resorcinol or other modifier, is a pale brown or straw color.

If in the above procedure of Paragraph 1, resorcinol is replaced with 1 part of 5-methoxyindole, an attractive light brown shade is obtained in 10 minutes.

When 1 part of the 5-amino-2,3-dimethylindole is dyed using the proportions of Example 4, paragraph one, in place of 5-aminoindazole, and no resorcinol, an attractive neutral light brown shade is obtained.

EXAMPLE 6

Direct Hair Dyeing Procedure

A mixture of 4 grams of a nonionic surfactant, polyoxyethylene (20) oleyl ether, 3 parts benzyl alcohol and 25 g. water is heated with stirring to 55° C. To this is added 0.1 g. of the dye compound. The whole is stirred 15 minutes at 55° C. Heat is removed, 75 g.

water added and the whole allowed to come to ambient temperature. The solution is divided into three equal portions, A, B, and C.

Solution A is adjusted to pH 4 with citric acid solution

Solution B is adjusted to pH 7 with standard NaOH—KH$_2$PO$_4$ buffer solution for pH 7

Solution C is adjusted to pH 9 with dilute ammonium hydroxide solution

Approximately 5 ml. of A, B, and C solutions are placed on separate watch glasses. A dry albino hair tress weighing about 250 mg. is placed in each solution and spread with a spatula. The hair tress is dyed for 5 minutes at ambient temperature. It is turned over, respread and dyed an additional 5 minutes. The tress is then removed, rinsed and dried in warm air.

The compound 5-bromo-7-nitroindoline, by this procedure, dyes hair a reddish yellow of good strength and good lightfastness, showing no change until 10 hours under Xenon arc light exposure. This compound is prepared by the method of Bennington, et al., J. Org. Chem. 27 142 (1962).

The compound 6-nitroindoline by this procedure, dyes hair a reddish yellow which is stable to light until 8 hours under Xenon-arc. It is prepared by the method of Terentier, et al., J. Gen. Chem. (USSR) 29 2504 (1959).

The compound 6-nitroindole by this procedure, dyes hair a green-yellow of fair strength.

EXAMPLE 7

Preparation of 5-amino-6-nitroindoline

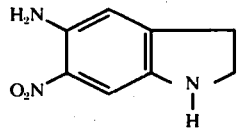

The synthesis starts with the known 1-acetyl-5-acetamidoindoline (A) Terentier, et al., J. Gen. Chem. (USSR) 2504 (1959); Chem. Abs. 59 10991C. To 4.36 g. of this compound in 75 ml. acetic anhydride at 10°–15° C. is added gradually over 30 minutes, 2 ml. fuming nitric acid d. 1.5. The whole is stirred 15 minutes more and drowned in ice. The product which is the 1-acetyl-5-acetamido-6-nitroindoline (B) is filtered and recrystallized from 600 ml. ethanol, a yellow solid, m. 213° C.

Product B is deacetylated by refluxing with 85 ml. conc. hydrochloric acid for 1 hr. 30 min. The whole is evaporated extracted with 400 ml. hot methanol, neutralized with excess ammonium hydroxide and filtered. The product is dissolved in 500 ml. ethyl acetate, treated with activated charcoal and saturated with HCl gas. The product is further purified by mixing with water and activated charcoal, and filtered. The filtrate containing the salt of the product is placed under nitrogen, neutralized with ammonium hydroxide solution, filtered, washed with water and dried to give a red solid 5-amino-6-nitroindoline, m. 190°–1.5° C. (D).

When dyed on hair by the method of Example 6, 5-amino-6-nitroindoline results in a light rust brown of good strength at all pH. The dyed hair has good levelness and crockfastness.

EXAMPLE 8

Preparation of 5,6-diaminoindoline-di-hydrochloride

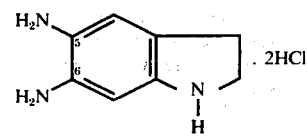

A mixture of 5 g. 1-acetyl-5-acetamido-6-nitroindoline, prepared as in Example 7 (B) and 75 ml. conc. hydrochloric acid solution is heated on a steam bath under nitrogen for 2 hours. The mixture is cooled to ambient temperature, placed in a Parr hydrogenation bottle together with 50 ml. water and 10% Pd on carbon (50 mg.). After shaking under 40 psi of hydrogen in a Parr apparatus for 1–2 hours (uptake-5.5 lb.) the solution is treated with activated charcoal, filtered, and evaporated to dryness. The residue is recrystallized from methanol-ethyl acetate 50/50 to give a pink solid, 4.15 g. 5,6-diaminoindoline dihydrochloride having a melting point in excess of 360° C.

When dyed on hair by the oxidation dyeing method of Example 2, a greenish-tan shade is obtained.

EXAMPLE 9

Preparation of 5,7-diaminoindoline dihydrochloride

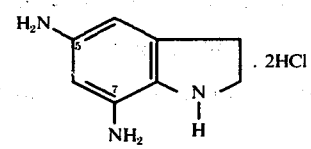

A mixture of 15 g. 1-acetyl-5,7-dinitroindoline, a known compound prepared by N. Rush, J. Org. Chem., 29 948 (1964), in 200 ml. conc. hydrochloric acid solution is heated under nitrogen for 1 hour on a steam bath. The mixture is cooled to ambient temperature and hydrogenated by the method of Example 8, with an uptake of 33 lb. hydrogen. The mixture is filtered and stripped to dryness. The residue is taken up in methanol under nitrogen, treated with activated charcoal and a filter aid and filtered. The filtrate is evaporated to a cloud point in a stream of nitrogen, stripped under vacuum, cooled and cold ethylacetate added. The product is isolated to give 8.86 g. 5,7-diaminoindoline dihydrochloride having a decomposition point above 270° C.

When dyed on hair by the oxidation dyeing method of Example 2, a pinkish-tan shade is obtained.

We claim:
1. A method for dyeing hair and other keratinaceous materials which comprises contacting said materials with a compound selected from the group consisting of 5-aminoindoline, 5,6-diaminoindoline, 5,7-diaminoindoline, 5-amino-6-nitroindoline, 5-bromo-7-nitroindoline, 5-hydroxyindoline, 6-nitroindoline, 5-aminoindole, 6-aminoindole, 5-hydroxyindole, 5-methoxyindole, 5-hydroxy-2-methylindole, 5-amino-2,3-dimethylindole, 6-nitroindole, and 5-aminoindole.
2. A method of claim 1 wherein the compound is 6-aminoindoline dihydrochloride.
3. A method of claim 1 wherein the compound is 5-bromo-7-nitroindoline.
4. A method of claim 1 wherein the compound is 5-aminoindole.
5. A method of claim 1 wherein the compound is 5-hydroxy-2-methylindole.
6. A method of claim 1 wherein the compound is 5-aminoindazole.
7. Keratinaceous material dyed by the method of claim 1.

* * * * *